United States Patent [19]

Oediger et al.

[11] 4,308,263
[45] Dec. 29, 1981

[54] PHOSPHONOFORMIC ACID HYDRAZIDE COMPOUNDS, THEIR PRODUCTION AND THEIR MEDICINAL USE

[75] Inventors: Hermann Oediger, Cologne; Folker Lieb, Leverkusen; Gert Streissle, Wuppertal, all of Fed. Rep. of Germany

[73] Assignee: Bayer Aktiengesellschaft, Leverkusen, Fed. Rep. of Germany

[21] Appl. No.: 161,542

[22] Filed: Jun. 20, 1980

[30] Foreign Application Priority Data

Jul. 3, 1979 [DE] Fed. Rep. of Germany ....... 2926799

[51] Int. Cl.$^3$ .......... A61K 31/16; C07F 9/38
[52] U.S. Cl. .................. 424/211; 260/501.12; 260/502.5; 260/944; 556/404; 556/405
[58] Field of Search ............ 260/502.5, 501.12; 424/211

[56] References Cited

U.S. PATENT DOCUMENTS

| | | | |
|---|---|---|---|
| 4,087,522 | 5/1978 | Von Esch | 424/211 |
| 4,092,412 | 5/1978 | Mao et al. | 424/212 |
| 4,150,125 | 4/1979 | Herrin et al. | 424/212 |
| 4,162,311 | 7/1979 | Razumov et al. | 424/211 |
| 4,215,113 | 7/1980 | Eriksson et al. | 424/212 |

FOREIGN PATENT DOCUMENTS

3008 7/1979 European Pat. Off. ............ 424/211

OTHER PUBLICATIONS

Herrin et al., "Journal of Medicinal Chemistry", 1977, vol. 20, No. 5, pp. 660–663.
Gerstein et al., "Antimicrobial Agents and Chemotherapy", Mar. 1975, pp. 285–288.

*Primary Examiner*—Joseph E. Evans
*Attorney, Agent, or Firm*—Sprung, Felfe, Horn, Lynch & Kramer

[57] ABSTRACT

The invention relates to phosphonoformic acid hydrazide compounds of the formula

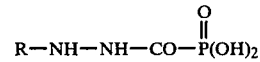

and salts thereof wherein R represents a hydrogen atom or a $C_1$–$C_6$-alkyl radical. The compounds are useful as antiviral agents, particularly against herpes viruses.

Also included in the invention are processes for preparing said phosphonoformic acid hydrazide compounds, compositions and medicaments containing said phosphonoformic acid hydrazide compounds and methods for the use of said compounds and compositions.

10 Claims, No Drawings

PHOSPHONOFORMIC ACID HYDRAZIDE COMPOUNDS, THEIR PRODUCTION AND THEIR MEDICINAL USE

The present invention relates to certain new phosphonoformic acid hydrazide compounds, to a process for their production and to their use as antiviral agents.

Antiviral agents are already known, for example agents from the substance class of nucleosides, such as 5-iodo-2′-desoxyuridin [see M. Negwer, Organisch-chemische Arzneimittel und ihre Synonyma (Organo-chemical medicaments and their synonyms), page 187, No. 1017; Akademie-Verlag, Berlin 1978], which have an action against herpes viruses. However, these agents frequently have undesired side effects, such as mutagenic, teratogenic or immunosuppresive effects.

Furthermore, for example, N-(1-adamantyl)-2-(2-dimethylaminoethoxy)-acetamide from the aminoamantane series has been disclosed [see DOS (German Published Specification) No. 1,941,218]. However, compared with known antiviral agents, this compound has only a weak action.

Phosphonoformic acid has also recently become known as an antiviral agent [see DOS German Published Specification) No. 2,728,685].

According to the present invention there are provided compounds which are phosphonoformic acid hydrazides of the formula $$R-NH-NH-CO-P(OH)_2 \text{ (I)}$$
$$\phantom{R-NH-NH-CO-}\overset{O}{\|}$$

or a salt thereof, in which
R represents a hydrogen atom or an alkyl
radical with 1 to 6 carbon atoms.

The new compounds of the present invention have powerful antiviral properties.

According to the present invention there is further provided a process for the production of compounds of the invention in which (a) a phosphonoformic acid ester of the general formula $$R_2O-CO-P(O-R_1)_2 \text{ (II)}$$
$$\phantom{R_2O-CO-}\overset{O}{\|}$$

in which
$R_1$ represents an alkyl radical and
$R_2$ represents an alkyl or aryl radical, is reacted with a trialkylsilyl halide of the formula $$(R_3)_3\text{Si-Hal} \text{ (III)}$$

in which
each $R_3$ independently represents an alkyl radical and
Hal represents a bromine or iodine atom, the resulting compound of the formula $$R_2O-CO-P(O-Si(R_3)_3)_2 \text{ (IV)}$$
$$\phantom{R_2O-CO-}\overset{O}{\|}$$

in which $R_2$ and $R_3$ have the above meaning, is reacted with water, and the resulting compound of the formula $$R_2O-CO-P(OH)_2 \text{ (V)}$$
$$\phantom{R_2O-CO-}\overset{O}{\|}$$

in which $R_2$ has the above meaning, in the form of a salt thereof, for example an alkali metal salt thereof, is reacted with a hydrazine of the formula $$R-NH-NH_2 \text{ (VI)}$$

in which R has the above meaning, or (b) from a phosphonoformic acid ester of the formula $$R_2O-CO-P(O-R_4)_2 \text{ (VII)}$$
$$\phantom{R_2O-CO-}\overset{O}{\|}$$

in which
$R_2$ has the above meaning and
$R_4$ represents an aralkyl radical, the radical $R_4$ is split off hydrogenolytically with hydrogen in the presence of a noble metal catalyst, and the resulting compound of the formula (V), as defined above, in the form of a salt thereof, for example an alkali metal salt thereof, is reacted with a hydrazine of the formula (VI), as defined above, or (c) a phosphonoformic acid ester of the formula (II), as defined above, is reacted with a hydrazine of formula (VI), as defined above, the resulting compound of the formula $$R-NH-NH-CO-P(O-R_1)_2 \text{ (VIII)}$$
$$\phantom{R-NH-NH-CO-}\overset{O}{\|}$$

in which R and $R_1$ have the above meanings, is reacted with silylating reagent, the resulting compound of the formula $$(R_3)_3\text{Si}-\underset{R}{\text{N}}-NH-CO-P(OR_1)_2 \text{ (IX)}$$

in which R, $R_1$ and $R_3$ have the above meanings, is reacted with a trialkylsilyl halide of the formula (III), as defined above, and the resulting compound of the formula $$(R_3)_3\text{Si}-\underset{R}{\text{N}}-NH-CO-P(O-Si(R_3)_3)_2 \text{ (X)}$$

in which R and $R_3$ have the above meaning, is reacted with water.

Surprisingly, the phosphonoformic acid hydrazides according to the invention exhibit a more specific antiviral efficacy and less sytotoxicity than the substance known from the state of the art. In substances according to the invention thus represent an enrichment of pharmacy.

If, in the course of the reaction variant (a), dimethoxyphosphonoformic acid methyl ester and trimethylsilyl iodide, sodium hydroxide solution, for the neutralisation, and hydrazine are used as the starting substances, the course of the reaction variants (a) (b) and (c) are illustrated by equations [A], [B] and [C], respectively.

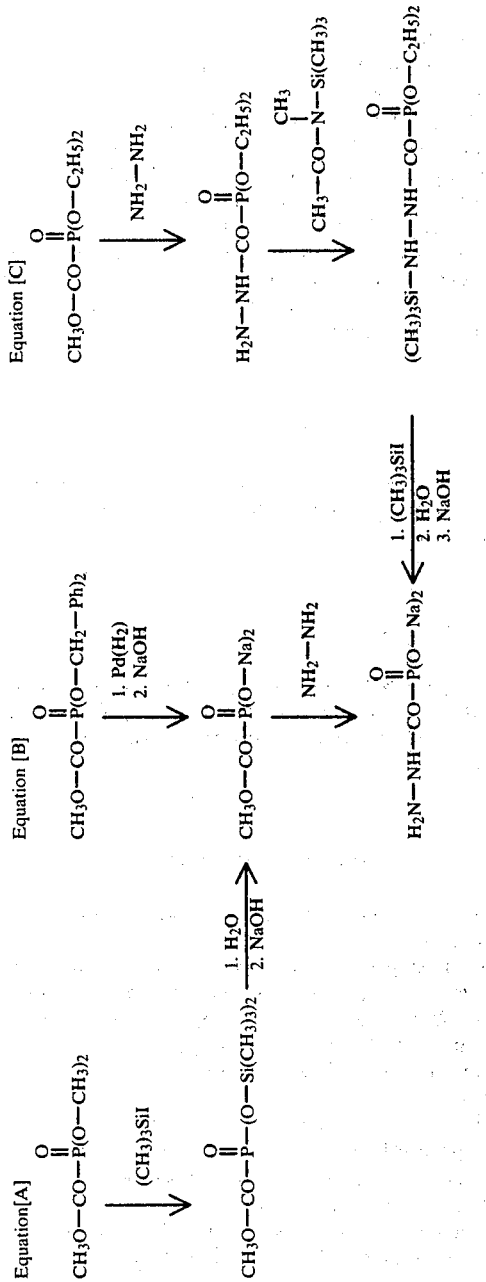

The phosphonoformic acid esters used as starting substances are known [Houben-Weyl, Methoden der organischen Chemie (Methods of organic Chemistry), volume XII/1, page 456].

Preferably, in the formula (II), R represents an alkyl radical with 1 to 4 carbon atoms, especially a methyl or ethyl radical, and $R_2$ represents an alkyl radical with 1 or 2 carbon atoms, especially a methyl radical, or an aryl radical, especially an optionally substituted phenyl radical substituted by lower alkyl, especially methyl, halogen, especially chlorine.

Examples which may be mentioned are: dimethoxyphosphonoformic acid methyl ester, diethoxyphosphonoformic acid methyl ester, dimethoxyphosphonoformic acid ethyl ester, diethoxyphonoformic acid ethyl ester, dimethoxyphosphonoformic acid phenyl ester and diethoxyphosphonoformic acid phenyl ester.

The trialkylsilyl halides used as starting substances are likewise known.

Preferably, in the formula (III), $R_3$ represents an alkyl radical with 1 to 4 carbon atoms, especially methyl, it also being possible for the alkyl groups to differ from one another, and Hal represents a bromine or iodine atom, preferably an iodine atom if $R_1$ represents an ethyl radical.

In the reaction with the trialkylsilyl halide, it is not necessary, for example, to add the trialkylsilyl iodides as such. It is sufficient, for example, to prepare these compounds in situ from the corresponding trialkylsilyl chlorides and sodium bromide of iodide, in the presence of the phosphonoformic acid esters of the general formula (II).

Possible diluents are organic solvents which are inert towards the reactants. Suitable solvents are hydrocarbons, aliphatic or cycloaliphatic hydrocarbons, such as cyclohexane, halogenated hydrocarbons, such as, for example, carbon tetrachloride, or aromatic hydrocarbons, (for example toluene), or alkane-carboxylic acid nitriles with 2 to 4 carbon atoms (for example propionitrile and preferably acetonitrile).

This initial process step of reaction variant (a) is generally carried out in a temperature range of between +10° C. and +80° C., preferably of between +20° C. and +70° C. In general, 1 mol of the compound (II) is reacted with 2.0 to 3.0, preferably with 2.0 to 2.2, mols of the compound (III). A larger excess of (III) does no harm, but is uneconomic. The reaction time depends on the temperature and the starting compounds employed and is between 15 minutes and 3 hours.

The compound of the formula (IV) is reacted with water, as illustrated in equation [A]. This process step of reaction variant (a) is generally carried out in a temperature range of between zero and +40° C., preferably of between +20° C. and +30° C. In general, 1 mol of the compound (IV) is reacted with at least 2 mols of water, and appropriately with a larger excess of about 30 mols of water. The reaction time depends on the temperature and on the structure of the silyl group and is in general between 1 minute and 10 minutes.

The resulting compound of the formula (V) is in general isolated in the form of an alkali metal salt, thereof, for example as a lithium salt or sodium salt thereof, for example by adding a sufficient amount of aqueous lithium hydroxide solution or sodium hydroxide solution and evaporating the mixture.

The compound of the formula (V) in the form of an alkali metal salt thereof, is reacted with a hydrazine of the general formula (VI), as illustrated in equation [A].

Preferably, in the formula (VI), R represents a hydrogen atom or an alkyl radical with 1 to 6 carbon atoms, in particular a hydrogen atom or an alkyl radical with 1 to 4 carbon atoms.

Examples which may be mentioned are: hydrazine, methylhydrazine, ethylhydrazine, propylhydrazine, butylhydrazine and hexylhydrazine.

The hydrazine can be employed in this reaction as such or, for example, also in the form of its aqueous solution. Possible diluents are, above all, water and/or water-miscible organic solvents which are inert towards the reactants. Suitable solvents are, above all, aliphatic alcohols with 1 to 4 carbon atoms, for example methanol or ethanol.

This process step of reaction variant (a) is generally carried out in a temperature range from +10° to +80° C., preferably between +20° and +60° C.

In general 1 mol of the compound (V), for example in the form of an alkali metal salt thereof, is reacted with 1 to 5 mols, preferably with 2 to 4 mols, of a hydrazine.

The reaction time depends on the temperature and is in general between 2 hours and 8 hours.

If dibenzyloxyphosphonoformic acid methyl ester is used as the starting substance in the course of the reaction variant (b), the course of the reaction variant (b) is illustrated by equation [B].

As illustrated by equation [B], an aralkyloxyphosphonoformic acid ester of the formula (VII) is split hydrogenolytically with hydrogen in the presence of a noble metal in the first step of process variant (b).

The aralkyloxyphosphonoformic acid esters used as starting substances are essentially unknown.

However, they can be prepared by known methods, for example from trisaralkyl phosphite with halogenoformic acid esters [see Houben-Weyl: Methoden der organischen Chemie (Methods of organic Chemistry), volume XII/1, page 456, Georg Thieme Verlag, Stuttgart 1963].

Preferably, in the formula (VII) $R_2$ represents an alkyl radical with 1 or 2 carbon atoms, especially a methyl radical or an aryl radical, especially an optionally substituted phenyl radical, and $R_4$ represents optionally substituted aralkyl radical, especially a benzyl radical.

Examples which may be mentioned are: dibenzyloxyphosphonoformic acid methyl ester, dibenzyloxyphosphonoformic acid ethyl ester, and dibenzyloxyphosphonoformic acid phenyl ester.

Finely divided palladium is a particularly suitable noble metal.

Possible diluents are, above all, organic solvents which are inert towards the reactants. Suitable solvents are, above all, aliphatic alcohols (such as alkanols) with 1 to 4 carbon atoms (such as methanol or ethanol), aliphatic esters (such as alkyl ester of alkanoic acids) with 3 to 8 carbon atoms (such as ethyl acetate), or mixtures of the solvents mentioned.

This process step of reaction variant (b) is generally carried out in a temperature range of from +20° C. to +150° C., preferably between +30° C. and +100° C.

The reaction can be carried out under normal pressure or also under increased pressure. In the latter case, it is in general carried out under pressures between 2 and 100 bars, preferably between about 5 and 50 bars.

The resulting phosphonoformic acid ester of the formula (V) is isolated, for example, in the form of a salt thereof, such as an alkali metal salt thereof, for example by adding a sufficient amount of aqueous lithium hydroxide solution or sodium hydroxide solution and evaporating the misture and, as illustrated in equation [B], is reacted with a hydrazine, according to the third step of reaction variant (a) as illustrated in equation [A].

If, in the course of the reaction variant (c), diethoxyphosphonoformic acid methyl ester is used as the starting substance, N-methyl-trimethylsilylacetamide is used as the silylating reagent and trimethyliodosilane is used to split the phosphono ester, the course of the reaction variant (c) is illustrated by equation [C].

As illustrated by equation [C], a dialkoxyphosphonoformic acid ester of the general formula (II) is reacted with a hydrazine of the formula (VI) in the first step of the process variant (c).

In the formula (II) preferably $R_1$ represents an alkyl radical which 1 to 4 carbon atoms, especially methyl or ethyl, most especially an ethyl radical, and $R_2$ represents an alkyl radical with 1 to 4 carbon atoms, especially methyl or ethyl, most especially methyl, or an aryl radical especially an optionally substituted phenyl radical, it is not necessary to employ anhydrous hydrazine. The hydrazine can also be employed, for example, in the form of an aqueous solution.

Possible diluents are, above all, water-miscible organic solvents which are inert towards the reactants. Suitable solvents are, above all, aliphatic alcohols (such as alkanols) with 1 to 4 carbon atoms, for example methanol or ethanol.

This process step or reaction variant (c) is generally carried out in a temperature range from 0° to 40° C., preferably between +10° and +30° C.

In general, 1 mol of the compound (II) is reacted with 1.0 to 1.2 mols, preferably 1.0 to 1.1. mols of the hydrazine. The reaction time depends on the temperature and is between 2 and 10 hours.

As illustrated by equation [C], the resulting compound of the general formula (VIII) is reacted with a silylating reagent in a second step of the process variant (c).

Suitable silylating reagents are, above all, those silyl compounds which, after transfer of the silyl group to the compound (VIII), are inert to other reactants in the further course of the sequence of stages, so that isolation of (IX) becomes unnecessary. Such silyl compounds include, for example, mono- or bis-silylated $C_1$–$C_6$ alkanecarboxylic acid amides, such as N,O-bis-trimethylsilylacetamide, N-trimethylsilyl-N-methylacetamide or N-trimethylsilylacetamide, in particular N-trimethylsilyl-N-methyl-acetamide.

Possible diluents are, above all, organic solvents which are inert towards the reactants. Suitable solvents are, above all, hydrocarbons, such as halogenated hydrocarbons (for example carbon tetrachloride or chloroform) or aromatic hydrocarbons (for example toluene), cyclic ethers (for example tetrahydrofurane or dioxane), or alkanecarboxylic acid nitriles with 1 to 4 carbon atoms (for example propionitrile and preferably acetonitrile).

The process according to the invention is generally carried out in a temperature range between +20° and +80° C., preferably between +30° and +70° C.

In general, 1 mol of the compound (VIII) is reacted with 1 to 3 mols of silylating reagent, preferably with 1 to 2 mols. A larger excess does no harm.

The reaction time depends on the temperature and is between 15 minutes and 2 hours.

It is not necessary to isolate the compound (IX), for example by evaporating off the diluent, but it can be further reacted directly in a suitable diluent.

As illustrated in equation [C], the resulting compound of the formula (IX) is then reacted with a trialkylsilyl halide of the formula (III), according to the first step of reaction variant (a) as illustrated in equation [A], the resulting silylated phosphonoformic acid hydrazide is reacted with water, according to the second step of reaction variant (a) as illustrated in equation [A], and the resulting phosphonoformic acid hydrazide is isolated, for example in the form of a salt thereof, for example in the form of an alkali metal salt thereof, for example by adding a sufficient amount of aqueous sodium hydroxide solution and evaporating the mixture.

The phosphonoformic acid hydrazides according to the invention have an action against viruses, in particular against herpes viruses.

Among the new phosphonoformic acid hydrazide salts of the invention, those salts that are pharmaceutically acceptable are particularly important and are preferred.

The new free phosphonoformic acid hydrazides of the formula (I) and their salts can be interconverted in any suitable manner; methods for such interconversion are known in the art.

The new active compounds can be employed as such or in the form of physiologically acceptable salts, for example salts with organic amines (such as triethylamine, cyclohexylamine or triethanolamine), or salts with inorganic, preferably alkali or alkaline earth metal, cations (for example lithium, sodium, potassium magnesium, calcium, zinc or ammonia).

As stated above the invention also relates to the use in medicine of the compound of the invention.

The present invention provides a pharmaceutical composition containing as active ingredient a compound of the invention in admixture with an inert pharmaceutical carrier, such as a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions, and emulsions of the active ingredient in aqueous or non-aqueous diluents or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $c_{16}$-fatty acid]) or mixtures of these diluents.

The pharmaceutical compositions which are solutions and emulsions can, for example contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 10% of the active ingredient by weight of the total composition; aqueous solutions for example buffered solutions with a pH of 6 to 8, being particularly suitable.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape of packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily does for administration of the medicaments of the invention is 500 mg to 50 g of active ingredient.

The product of the above-mentioned pharmaceutical compositions and medicaments is carried out by any method known in the art, for example, by mixing the active ingredient(s) with the inert pharmaceutical carrier to form a pharmaceutical composition (e.g. a granulate) and then forming the composition into the medicament (e.g. tablets).

This invention further provides a method combating (including prevention, relief and cure of) the above-mentioned diseases in warm-blooded animals, which comprises administering to the animals a compound of the invention alone or in admixture with a diluent or in the form of a medicament according to the invention.

It is envisages that these active compounds will be administered perorally, parenterally (for example intramuscularly, intraperitoneally, subcutaneously and intravenously) or rectally, preferably parenterally or orally. Preferred pharmaceutical compositions and medicaments are therefore those adapted for administration such as parenteral or oral administration. Administration in the method of the invention is preferably parenteral or oral administration.

In general, it has proved advantageous to administer amounts of from 10 mg to 1,000 mg/kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate processes for the production of compounds of the present invention.

EXAMPLE 1

The Na$_2$ salt of phosphonoformic acid methyl ester 22.5 parts by weight of sodium iodide are dissolved in 90 parts by volume of acetonitrile, and 12.6 parts by weight of dimethoxyphosphonoformic acid methyl ester are added at 25° C. 17.0 parts by weight of trimethylchlorosilane are allowed to run into the solution at 25° C., whilst cooling, the mixture is then stirred at 25° C. for 30 minutes and subsequently at 40° C. for 15 minutes, the sodium chloride which has precipitated is removed by filtration or centrifugation and the solution is evaporated in vacuo. The evaporation residue is taken up in 30 parts by volume of water and the resulting aqueous solution is neutralised with dilute sodium hydroxide solution and then evaporated in vacuo. After triturating the residue with acetone and isolating the crystals by filtration, 14.8 parts by weight of the Na$_2$ salt of phosphonoformic acid methyl ester, as the hydrate, are obtained (yield 98%)

EXAMPLE 2

The Na$_2$ salt of phosphonoformic acid hydrazide 36.8 parts by weight of the Na$_2$ salt of phosphonoformic acid methyl ester are suspended in 280 parts by volume of methanol, and 40.0 parts by weight of hydrazine hydrate and an amount of water such that a solution was formed are added at +5 to +10° C. The mixture is stirred at 25° C. for 2 hours and subsequently at 60° C. for 4 hours and is allowed to cool and the reaction product which has precipitated is filtered off. After washing with methanol, 30.0 parts by weight of the Na$_2$ salt of phosphonoformic acid hydrazide are obtained (Yield 81%). $^{13}$C-NMR(D$_2$O): $\delta = 178.3$ ppm (doublet, D=0); $I_{P,C} = 190$ HZ.

EXAMPLE 3

Diethoxyphosphonoformic acid hydrazide 19.6 parts by weight of diethoxyphosphonoformic acid methyl ester are diluted with 10 parts by volume of ethanol, and a solution of 5.0 parts by weight of hydrazine hydrate in 10 parts by volume of ethanol is added at +10 to +20° C. The mixture is stirred at room temperature for 8 hours, the solvent is moved in vacuo and 19.4 parts by weight (yield 99%) of crude diethoxyphosphonoformic acid hydrazide, which is further processed without purification, are obtained.

EXAMPLE 4

The Na$_2$ salt of phosphonoformic acid hydrazide 18.0 parts by weight of N-trimethylsilyl-N-methylacetamide are allowed to run into a solution of 9.7 parts by weight of diethoxyphosphonoformic acid hydrazide in 90 parts by volume of anhydrous acetonitrile at room temperature the reaction mixture is stirred at 50° for 15 minutes and subsequently at 70° for 5 minutes and then cooled to 20° C. and 15 parts by weight of sodium iodide are added at this temperature. A solution of 12 parts by weight of trimethylchlorosilane in 30 parts by volume of acetonitrile is then allowed to run in, the mixture is stirred at 25° C. for 30 minutes and subsequently at 40°-45° C. for 2 hours and then cooled to 25° C., the sodium chloride which has precipitated is removed by filtration or centrifugation and the solution is evaporated in vacuo.

The evaporation residue is taken in 30 parts by volume of water and the resulting aqueous solution is neutralised immediately with dilute sodium hydroxide solution and then evaporated in vacuo. After triturating the residue with methanol and isolating the crystals by filtration, 6.6 parts by weight of the Na$_2$ salt of phosphonoformic acid hydrazide with the analytical data described in Example 2 are obtained (yield: 72%).

EXAMPLE 5

The Na$_2$ salt of phosphonoformic acid phenyl ester 60 parts by weight of sodium iodide are dissolved in 360 parts by volume of acetonitrile, and 51.6 parts by weight of diethoxyphosphonoformic acid phenyl ester are added at 25° C. 48 parts by weight of trimethylchlorosilane are allowed to run into this solution at 25° C., whilst cooling, the mixture is then stirred at 25° C. for 30 minutes and subsequently at 40° C. for 15 minutes, the sodium chloride which has precipitated is then removed by filtration or centrifugation and the solution is evaporated in vacuo.

The evaporation residue is taken up in 120 parts by volume of water and, after separating off the hexamethyldisiloxane formed, the resulting solution is neutralised with dilute sodium hydroxide solution and then evaporated in vacuo. After triturating the residue with acetone and isolating the crystals by filtration, 45.3 parts by weight of the Na$_2$ salt of phosphonoformic acid phenyl ester are obtained (yield 92%).

EXAMPLE 6

The Na$_2$ salt of phosphonoformic acid hydrazide 24.6 parts by weight of the Na$_2$ salt of phosphonoformic acid phenyl ester are dissolved in 70 parts by volume of water, and 15.0 parts by weight of hydrazine hydrate are added at +15° to +20° C. The mixture is stirred at 25° C. for one hour and at 65° C. for 3 hours and allowed to cool, the phenol formed is removed by extraction with ether and the aqueous solution is evaporated in vacuo. After triturating the residue with methanol and isolating the crystals by filtration, 18.4 parts by weight of the Na$_2$ salt of phosphonoformic acid hydrazide are obtained (yield 100%).

EXAMPLE 7

The Li$_2$ salt of phosphonoformic acid phenyl ester 25.8 parts by weight of diethoxyphosphonoformic acid phenyl ester are dissolved in 80 parts by volume of acetonitrile, and 36.7 parts by weight of trimethylbromosilane are added at 20° C. The mixture is stirred at 40°-45° C. for 2 hours and the solution is then evaporated in vacuo. The evaporation residue is taken up in 60 parts by volume of water and, after separating off the hexamethyldisiloxane formed, the resulting solution is neutralised with dilute lithium hydroxide solution and then evaporated in vacuo.

After triturating the residue with acetone and isolating the crystals by filtration, 20 parts by weight of the Li$_2$ salt of phosphonoformic acid phenyl ester are obtained (yield 93%).

EXAMPLE 8

The Li$_2$ salt of phosphonoformic acid hydrazide 8.6 parts by weight of the Li$_2$ salt of phosphonoformic acid phenyl ester are dispersed in 86 parts by volume of water, and 8.0 parts by weight of hydrazine hydrate are added at 20° C. The mixture is stirred at 25°

C. for one hour and at 60° C. for 3 hours and allowed to cool, the phenol formed is removed by extraction with ether and the aqueous solution is evaporated in vacuo. After triturating the residue with methanol and isolating the crystals by filtration, 5.5. parts by weight of the Li₂ salt of phosphonoformic acid hydrazide are obtained (yield 90%).

EXAMPLE 9

The Na₂ salt of phosphonoformic acid methyl hydrazide 46 parts by weight of Na₂-salt of phosphonoformic acid methyl ester are dissolved in 90 parts by volume of water and 46 parts by weight of methyl hydrazine are added at 25° C. The mixture is stirred at 80° C. for 7 hours and allowed to cool. The residue is removed by suction filtration and the filtrate is evaporated in vacuo. The residue after evaporation is digested with ethyl alcohol and the such obtained crystals are again dissolved in a mixture of 70 parts by volume methanol and 200 parts by volume ethyl alcohol and thereafter precipitated. 90 parts by weight of Na₂-salt of phosphonoformic acid methyl hydrazide are obtained (yield 38%).

EXAMPLE 10

Diethanol ammonium salt of phosphonoformic acid hydrazide 4.4 parts by weight of phosphonoformic acid hydrazide are run in 20 parts by volume of water and neutralised by a 2 molar solution of diethanol amine in water. The resulting solution is evaporated, the evaporation residue is triturated with a mixture of ethanol and methanol (90 parts by volume plus 10 parts by volume) and the crystals are isolated 11 parts by weight of diethanol ammonium salt of phosphonoformic acid hydrazide are obtained (yield 100%).

EXAMPLE 11

Phosphonoformic acid hydrazide 20 parts by weight of Na₂ salt of phosphonoformic acid hydrazide are dissolved in 60 parts by volume of water and an equivalent amount of 4 n hydrochloric acid is added. The residue is isolated by filtration, washed with water and dried. 12.6 parts by weight of phosphonoformic acid hydrazide are obtained (yield 90%).

The following tests were carried out to evaluate the antiviral activity of phosphonoformic acid hydrazide.

1. Cell culture tests

The antiviral activity of phosphonoformic acid hydrazide was tested in the plaque reduction test according to E. C. Herrmann (Proc. Soc. Exp. Biol. Med. 107, 142–145, 1969). Untreated virus-infected and non-infected cell cultures served as control. In addition, the cytotoxic activities of the compound were measured.

(a) Antiviral activity

Cells from rabbit kidneys cultivated in plastic dishes are infected with herpes simplex virus. After virus absorption for 45 minutes at 37° C. in a CO₂-incubator the cells are covered with an overlay which consists of cell culture medium plus Sephadex G 200. The overlay contains the test compound in various concentrations. After additional incubation for 48–72 hours at 37° C. the cells are fixed and stained with Giemsa. The virus plaques are counted and the compound-induced reduction of the plaque number is determined. The results which were obtained with phosphonoformic acid hydrazide and phosphonoformic acid are listed in Table 1.

(b) Cytotoxic activity

Culture medium with different concentrations of the test compound is added to confluent cell cultures. Control cultures receive the culture medium without test compound. After incubation for 48 hours at 37° C. the culture medium is removed and nutrient medium without test compound is added to all cell cultures. After additional incubation for two days at 37° C. the number of cells per culture dish is determined and the reduction of cell numbers (e.g. the inhibition of cell multiplication) is calculated in the treated culture as compared to untreated ones (Table 2).

The results demonstrate, that phosphonoformic acid hydrazide shows antiviral activity in vitro which is comparable to that of phosphonoformic acid. However, phosphonoformic acid hydrazide is better tolerated by the cells than phosphonoformic acid especially at higher concentration.

TABLE 1

| | Plaque reduction test | | | | | | |
|---|---|---|---|---|---|---|---|
| | | | dilution (g/ml) | | | | |
| Compound | 10g | 10⁻²·⁵ | 3,0 | 3,5 | 4,0 | 4,5 | 5,0 |
| phosphonoformic acid hydrazide | | 3 | 3 | 1 | 1 | 0 | 0 |
| sodium salt of phosphonoformic acid | | + | 3 | 2 | 2 | 1 | 0 |

+ = cytotoxic
0 = without activity
1 = 25% reduction of virus plaques
2 = 25–75% reduction
3 = 75–100% reduction

TABLE 2

| | Inhibition of cell multiplication | | |
|---|---|---|---|
| | Reduction of the number of cells by incubation of the cell cultures in compound-containing medium for 24 hours | | |
| Compound | 30% | 50% | 70% |
| phosphonoformic acid hydrazide | 620⁽⁺⁾ | 1.620⁽⁺⁾ | 4.200⁽⁺⁾ |
| sodium salt of phosphonoformic acid | 450⁽⁺⁾ | 1.000⁽⁺⁾ | 1.800⁽⁺⁾ |

(+) = μ/ml

The present invention also comprises pharmaceutically acceptable bioprecursors of the active compounds of the present invention.

For the purpose of this specification the term "pharmaceutically acceptable bioprecursor" of an active compound of the invention means a compound having a structural formula different from the active compound but which nonetheless, upon administration to a warm-blooded animal is converted in the animal's body to the active compound.

What is claimed is:

1. A compound which is a phosphonoformic acid hydrazide of the formula

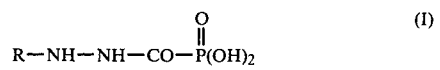

R—NH—NH—CO—P(OH)₂  (I)
            ‖
            O or a salt thereof, in which

R represents a hydrogen atom or an alkyl radical with 1 to 6 carbon atoms.

2. A compound of claim 1 which is the $Na_2$ salt of phosphonoformic acid hydrazide.

3. A compound of claim 1 which is the $Li_2$ salt of phosphonoformic acid hydrazide.

4. A pharmaceutical composition which comprises an antivirally effective amount of a compound according to claim 1 in admixture with an inert pharmaceutical carrier.

5. A pharmaceutical composition of claim 4 in the form of a sterile or physiologically isotonic aqueous solution.

6. A medicament in dosage unit form comprising an antivirally effective amount of a compound of claim 1 together with an inert pharmaceutical carrier.

7. A medicament of claim 6 in the form of tablets, pills, dragees, capsules, ampoules, or suppositories.

8. A method of combating virus illnesses in warm-blooded animals which comprises administering to the animals an active compound according to claim 1 either alone or in admixture with an inert pharmaceutical carrier.

9. A method according to claim 8 in which the active compound is administered in an amount of 10 mg to 1,000 mg per ky body weight per day.

10. A method according to claim 9 in which the active compound is administered parenterally or orally.

* * * * *